(12) United States Patent
Guth et al.

(10) Patent No.: US 9,144,376 B2
(45) Date of Patent: Sep. 29, 2015

(54) SENSOR SYSTEM FOR DETERMINING THE CONTROL SIGNALS ACTIVATING CILIARY MUSCLES

(71) Applicant: KARLSRUHER INSTITUT FUER TECHNOLOGIE, Eggenstein-Leopoldshafen (DE)

(72) Inventors: Helmut Guth, Eggenstein-Leopoldshafen (DE); Ulrich Gengenbach, Remchingen (DE); Georg Bretthauer, Karlsruhe (DE); Jan Fliedner, Karlsruhe (DE); Christoph Beck, Karlsruhe (DE); Markus Krug, Karlsruhe (DE); Thomas Martin, Karlsruhe (DE); Joerg Nagel, Eggenstein-Leopoldshafen (DE); Liane Koker, Stutensee (DE); Ingo Sieber, Karlsruhe (DE)

(73) Assignee: KARLSRUHER INTITUT FUER TECHNOLOGIE (KIT), Karlsruhe (DE)

( * ) Notice: Subject to any disclaimer, the term of this patent is extended or adjusted under 35 U.S.C. 154(b) by 0 days.

(21) Appl. No.: 14/151,781

(22) Filed: Jan. 9, 2014

(65) Prior Publication Data
US 2014/0192318 A1    Jul. 10, 2014

(30) Foreign Application Priority Data
Jan. 10, 2013 (DE) .......................... 10 2013 000 429

(51) Int. Cl.
| A61B 3/10 | (2006.01) |
| A61B 3/00 | (2006.01) |
| G02C 7/08 | (2006.01) |
| A61B 3/09 | (2006.01) |
| A61B 5/0496 | (2006.01) |
| A61B 5/00 | (2006.01) |
| A61F 2/16 | (2006.01) |
| A61B 5/11 | (2006.01) |

(52) U.S. Cl.
CPC ... *A61B 3/10* (2013.01); *A61B 3/09* (2013.01); *A61B 5/0496* (2013.01); *A61B 5/6821* (2013.01); *G02C 7/083* (2013.01); *A61B 5/1107* (2013.01); *A61F 2/16* (2013.01)

(58) Field of Classification Search
USPC .................................................. 351/200–246
See application file for complete search history.

(56) References Cited

U.S. PATENT DOCUMENTS

2005/0280777 A1*  12/2005  Dai ................................ 351/246
2014/0240665 A1*   8/2014  Pugh et al. .................... 351/205

* cited by examiner

*Primary Examiner* — Mohammed Hasan
(74) *Attorney, Agent, or Firm* — Klaus J. Bach

(57) ABSTRACT

In a sensor system for determining the control signal supplied to the ciliary muscles of an eye for adjusting the focal length of the lens of an eye, a contact element of an electrically non-conductive material and provided with sensors is disposed on the cornea of the eye so that the sensors are arranged in contact with an annular area of the cornea next to the ciliary eye muscles so as to be able to sense the focal adjustment signals supplied to the ciliary muscles and the sensed adjustment signals are supplied to a signal processing unit which provides a control signal to a lens system with adjustable focal length for adjusting the focal length thereof depending on the focal adjustment signals of the ciliary eye muscles.

10 Claims, 6 Drawing Sheets

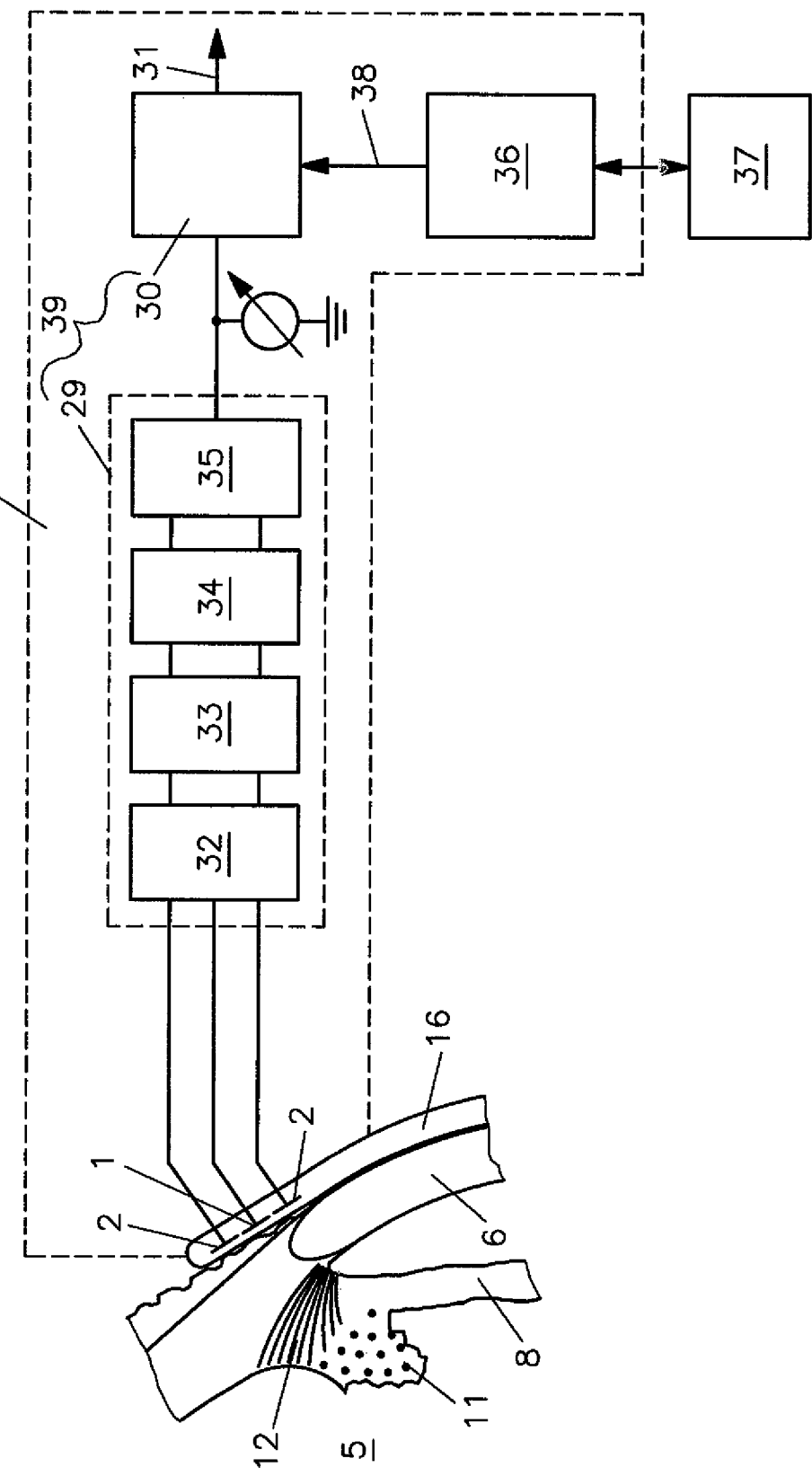

SENSOR SYSTEM FOR DETERMINING THE CONTROL SIGNALS ACTIVATING CILIARY MUSCLES

The invention resides in a sensor system for determining the control signals activating the ciliary muscles of an eye via a contact element which is disposable on the cornea around the iris of an eye and consists of an electrically nonconductive material on which sensors are arranged in an annular array and a signal processor arranged on or in the contact element.

The sensor system includes furthermore an evaluation system for determining the accommodation needs of an artificial accommodation system preferably of an artificial lens or an ophthalmic technical system.

The human eye is a natural optical system which depicts objects on the retina by way of several light refracting boundary surfaces with sharp definition. When the distance of the object being observed changes, the imaging conditions of the optical system need to adapt to maintain the sharp definition of the object. In the human eye, this is accomplished by a deformation of the lens by means of the ciliary muscle (musculus ciliaris) whereby essentially the shape of the front and the rear surfaces, that is, the curvature of the lens is changed (accommodation).

However, with increasing age, the human eye loses its capability for accommodation, that is, the capability of the natural lens system to adapt to different distances by adjusting the curvature or focal length of the lens. In the healthy eye, the focal length is changed in that the above mentioned curvature of the lens is changed by changing the radius of curvature of the lens surfaces by activation of the ciliary muscles whereby the degree of refraction is changed. However, with increasing age, the natural lens becomes stiffer and can no longer change its radius of curvature sufficiently to provide for different focal lengths. This loss is compensated for with viewing aids such as glasses, the person suffers from presbyopia.

However, even when, with increasing age, the human eye lens becomes more rigid and can no longer adjust to different viewing distances, the ciliary muscle remains active. In [1] it is described that the age affects the ciliary muscle activity only slightly, that is, that the ciliary muscle activity decreases with increasing age but never disappears completely. Independent thereof are the control signals for the ciliary muscles which remain essentially unchanged with increasing age.

Another reason for the loss of the accommodation capability is the cataract. With this condition, the natural lens becomes cloudy to an extent that a person becomes blind. For the treatment of this condition at this point, an artificial intraocular lens is implanted into the respective eye which however has a fixed focal length, but at least transparency is re-established. Because of its fixed curvature, an accommodation of the eye is not possible although the control signals are still supplied to the ciliary muscles.

In order to compensate for a missing accommodation capability of the natural eye, various attempts to develop accommodating ophthalmic technical systems have become known. Besides an artificial accommodation system which includes an implant installed, see [23], like an intraocular lens into the eye, also actively accommodating systems are being developed as integral parts of contact lenses or glasses; see [6-8]. Contact lenses have in comparison to implants into the lens cavity a relatively small volume and, accordingly have a smaller installation space for integrated active components. The arrangement of contact lenses on the cornea of the eye poses requirements which differ from those of systems installed in the lens cavity and also offer different possibilities for the realization of the sensor unit for determining the accommodation needs. With the aid of the information regarding the accommodation needs, the active optical system integrated into the contact lens can be adjusted to the focal length needed by a patient for viewing an object at a particular distance.

Determination of the accommodation needs of an eye is possible by a determination of the ciliary muscle activity. The control signals of the ciliary muscle can be detected via the electric activities of the muscles for example by potential measurements.

In practice, surface electrodes or muscles fine conductor electrodes in contact with, or implanted into, the muscle have been found suitable for determining the muscle activity. However, most known systems for measuring the muscle activity are limited to measuring larger muscle areas.

In [3], in connection with an implantable artificial accommodation system, the possibility is discussed to measure The muscle potential of the ciliary muscle from capsule cavity and to determine the accommodation needs in this way. It is pointed out that the measurable potential in the capsule cavity was too low because of the large distance of the implant from the ciliary body.

[4] discloses a testing arrangement for measuring potentials directly on the cornea of an eye. To this end, four electrodes are disposed directly on the cornea in the area of the iris wherein one of the electrodes has a direct contact with the cornea. The electrodes are provided with conductors which are connected via the open eye to a further signal processor.

[5] discloses a contact lens with four electrodes especially for a multi-dimensional determination of the ciliary muscle activity. The electrodes are arranged on the inner side of a contact lens ail at the same distance from the contact lens center point and also equally spaced from one another. The contacts to the electrodes are established by conductors disposed on the outside of the contact lens. Although this arrangement was intended for the exploration of the activity of the various muscle fibers of the ciliary body during accommodation, no separate detection of signals of individual fiber directions is provided for. The arrangement and the measuring principle do not permit a determination which of which muscle signals the measured signal is composed. As a result, it is for example not possible to distinguish between the activity of the ciliary muscles and the activity of the iris muscles. A reliable determination of the accommodation need is therefore greatly limited.

It is the object of the present invention to provide a sensor system for determining the control signals of a ciliary muscle of an eye with a directional resolution so that the signal is suitable for determining the accommodation needs of the eye.

SUMMARY OF THE INVENTION

In a sensor system for determining the control signal supplied to the ciliary muscles of an eye for adjusting the focal length of the lens of an eye, a contact element of an electrically non-conductive material and provided with sensors is disposed on the cornea of the eye so that the sensors are arranged in contact with an annular area of the cornea next to the ciliary eye muscles thereby to be able to sense the focal adjustment signals supplied to the ciliary muscles, and the sensed adjustment signals are supplied to a signal processing unit which provides a control signal to a lens system such as glasses or a contact lens with adjustable focal length for adjusting the focal length thereof depending on the focal adjustment signals of the ciliary muscles.

It is important that the control signals are actively applied to the ciliary muscles and these signals are detectable on the cornea of the eye; not at the capsule cavity which is more remote from the ciliary muscles. The ciliary muscle adjoins the area around the iris. Consequently, the sensor system comprises a contact element applied to the cornea around the iris of an eye.

If the contact element is a contact lens, not only the sensor system but also a complete ophthalmic technical system, preferably an artificial accommodation system including the sensor system mentioned earlier and an artificial lens with adjustable focal lengths or a lens system are disposed in the contact lens (active contact lens). Preferably, all the components required for a self-sufficient operation of the accommodation system are disposed on, or integrated into, the contact lens.

If the contact element is a contact ring, it extends preferably around the iris without covering the iris or the pupil. The sensor system detects in this embodiment only the eye control signals of the ciliary muscle, processes these signals to form a system control signal and supplies this system control signal preferably via corresponding transmission means (for example via electromagnetic waves or via conductors) to an independent ophthalmic technical system such as accommodating glasses or an implantable adjustable lens system. To this end, the control system comprises a signal processor with transmission means to a lens body or lens system whose focal length is adjustable by the control signal, wherein the transmitted signals do not necessarily comprise the control signal.

The ciliary muscle serves to adapt the lens in an eye to objects at different distances. The ciliary muscle comprises two groups of muscle fibers which are oriented differently and act independently of each other, the so-called Müller muscle whose fibers extend annularly around the lens of the eye that is tangentially to the iris, and the so-called Brück muscle whose fibers extend meridionally, that is, radially with respect to the axis of the lens. The Müller muscle extends around the lens and controls the radial contraction of the ciliary body. By a contraction, the zonula fibers are de-tensioned whereby the form and surfaces of the lens and, as a result, the focal length of the lens are changed. The Brück muscle is to change the axial position of the natural lens. The Müller muscle serves in particular for close-up accommodation, the Brück muscle is used for distance setting adjustment. An age-related decrease of the accommodation capability is not caused by a reduced muscle activity but rather by a stiffening of the eye lens.

In a state of rest, that is, when not subjected to control signals, the muscle establishes a rest potential of for example about −85 mV. During this state, sodium ions flow into the muscle cells and calcium ions flow out of the muscle cells. As a result, the cell potential changes for a short period of for example about 2 ms to for example 30 mV (depolarization), which, subsequently, rapidly drops again (re-polarization) and reaches again the rest potential via a counter oscillation (hyper-polarization). This excitation occurs within a period of about 2-4 m/s along a motorized nerve through the muscle, that is, in the muscle fiber direction. The potential change caused thereby can be measured providing an indication for the muscle activity.

An essential feature of the solution according to the invention is based on the possibility to selectively determine the control signals of the Müller and the Brück muscles which are characterized by their orientation around the iris. For this purpose sensors are proposed which comprise at least three electrodes oriented in at least one direction and arranged in series. The sensors include in each case a center electrode (reference electrode) and, at each side thereof, a measuring electrode disposed adjacent and parallel to the reference electrode. While a reference potential is applied to the center electrode, the at least two adjacent measuring electrodes detect the respective local adjacent potentials on the cornea. These sensor electrodes which are arranged preferably directly on the cornea determine in an advantageous way the electric potential differences relative to the center electrode (one measurement per electrode) selectively in the respective orientation. When a muscle fiber is stimulated by the application of a voltage, this voltage can be detected by potential differences present at the two measuring electrodes only if the fiber orientation is parallel to the sensor orientation. When a measurement error for example because of a displacement of the electrodes from the muscle fibers or by an orientation deviating from the fiber orientation can be detected by way of a larger deviation of the potential differences determined in a sensor in a particular direction, the particular measurement value can be eliminated by a subsequent signal processing for a control of for example an ophthalmic technical system.

In a preferred embodiment, the sensor system comprises at least two sensors with orientations extending in tangential as well as radial directions with respect to the iris. In this way, the signals of the muscle fibers oriented radially to the iris, that is the Brück muscles as well as the signals of the muscles oriented tangentially with regard to the iris, that is the Müller muscles, can be selectively determined.

A further improved selective determination can be achieved in that each sensor comprises either only a tangentially or only a radially oriented sensor, that is, no sensors deviating from a predetermined orientation. Preferably, the last mentioned sensors are arranged alternately in an annular array around the iris.

The sensor system comprises furthermore a signal processor which is disposed on the contact element. The sensors are in communication with the signal processor via sensor conductors for transmitting data. The signal processor comprises preferably a signal conditioning arrangement, a signal recognition arrangement and a generator for generating a control signal. The signal conditioning arrangement processes the raw data of the sensors, that is, in particular it serves the elimination of noise signals. It comprises, in addition to amplifier stages, in particular signal manipulating components such as filters and rectifiers. The signal recognition arrangement receives the conditioned raw data of the sensors and supplies them to a signal evaluation arrangement. On the basis of the conditioned signals a signal generator provides on one hand control signals for the sensors and the subsequent system such a technical ophthalmologic system with adjustable lenses or an artificial accommodation system, on the other hand. The signal evaluation arrangement supplies for each sensor the activation potential (control signal) for the respective muscle strands.

The signal evaluation arrangement compares and processes the raw sensor data so as to determine an activation value of the ciliary muscle (for example, position for near accommodation, mainly caused by the Müller muscle fibers, zero for the resting state and negative for the activation of the Brück muscle fibers for distant accommodation). It is an object of the signal evaluation to suppress in this way the disturbances or noise and the isolation of the cumulative muscle fiber signals for each of the Müller and the Brück muscle fiber strands. To this end, the signal evaluation needs preferably also all calibration data which can be transmitted via a communication interface.

The present invention is concerned furthermore with the use of the above-mentioned means for controlling (control or initiation) of an accommodation need determination and/or a focus adjustment for the ophthalmological technical system or an accommodation system as well as a method for controlling an ophthamological technical system or an accommodation system.

The evaluation of the muscle signals of the ciliary muscle has all the advantages of a pupil proximity reflex sensor such as the use of the body-inherent control circuit for the natural accommodation and the intuitive use by the system carrier. Noise effects such as incident light do not affect the ciliary muscle which promises a substantial increase in reliability. The relatively low complexity of the signal processing and evaluation of the ciliary muscle activity promises very low energy requirements for the measuring and evaluation system.

A pupil proximity reflex sensor detects a body reaction which may also comprise the issue of a signal of an accommodation control circuit. If such a signal can be determined selectively, that is, separate from the other pupil reactions (for example, effects of adrenaline, caffeine, tiredness, etc. . . . ) the body-based accommodation/focusing control circuit may be used for the determination of the accommodation needs. Part of the accommodation control can then be taken over by the brain after an adaption phase.

Sensors which for example determine the vergency angle between the fixation lines of the eyes can evaluate only the signals which originate mainly from the verging control circuit of the human brain. The vergency reaction however is sometimes very much time delayed and includes over-shootings, which detrimentally affect the sensor arrangement. In addition, the determination of the vergency angle is affected by external disturbances (for example, vibrations, acceleration sensor or distortions in the magnetic field of the earth, magnet field sensor).

An evaluation of the ciliary muscle activity is very advantageous since the system obtains direct access to the output signal of the accommodation control circuit of the brain, by the evaluation of the ciliary muscle activity. The accommodation needs do not need to be estimated in a complicated manner via detours but can be determined directly via the activation potential of the ciliary muscle. The evaluation of the ciliary muscle consequently offers the possibility to provide an artificial accommodation system or an artificially adjustable optical system with a dynamics comparable to a body's normal eye lens system with large evaluation and calculation efforts. In an advantageous way, the human brain can learn to adjust to the artificial system. Preferably only a simple basic calibration is performed while the fine calibration is left to the learning capability of the brain The sensor system, is basically useable for different applications.

Preferably, the sensor system is fully integrated in, or on, a contact lens. Herein, the sensors together with the signal processing arrangement as described and with an energy storage device and/or possibly other means or sources for the input of energy are accommodated in the edge area of the contact lens. In the center of the lens, there is an active optical system with variable refraction capability. The refraction capability can now be dynamically adapted to the accommodation needs determined by the above-described sensor system.

Alternatively, the sensor system comprises a preferably contact-free transmission means as interface to an external energy source and/or an external accommodating or adjustable lens system. By way of this interface, accommodation information can be transmitted to accommodating glasses or an accommodating ophthalmological system. The advantage of external components such as glasses as an adaptive optical element resides in the fact that a substantially larger installation space is available. Such glasses comprise preferably an optical element with variable refraction capability, a control unit for this optical element, an energy supply and also transmission means for the sensor system. The sensor system is supplied with energy preferably by means of the glasses. In this way, the energy storage of the sensor system as such can be reduced to an optional energy buffer that is its size can be significantly reduced.

Also advantageous is the use of the described sensor unit in combination with an active implantable accommodation system or an active intraocular lens (IOL). On one hand, the installation space for a sensor system in the installation space-critical IOL can be saved. On the other hand, the disadvantages of the known sensor concepts such as the convergence angle measurement or pupil proximity reflex for determining the accommodation needs without utilization of the ciliary muscle signals are eliminated. The IOL includes the same elements as the accommodating glasses referred to above that is an optical element with variable refraction capability, a control unit, an energy storage device or source and transmission means.

The invention and details and embodiment options thereof will become more readily apparent from the following description of particular embodiments with reference to the accompanying drawings which may include some or all of the features mentioned earlier.

BRIEF DESCRIPTION OF THE DRAWINGS

FIG. 4 shows a diagram of a sensor circuitry including the sensors and the sensor signal processing system.

DESCRIPTION OF PARTICULAR EMBODIMENTS

Figure 1A:
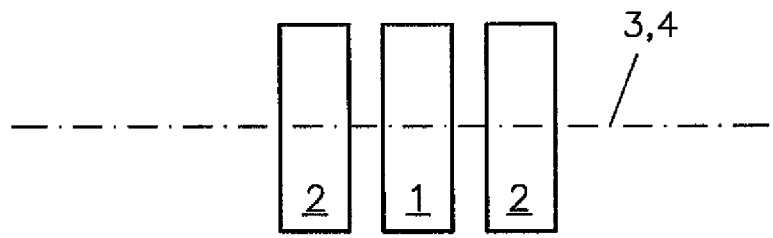
FIGS. 1a, 1b and 1c are schematic representations of exemplary embodiments of a sensor of the sensor system.
Figure 1B:
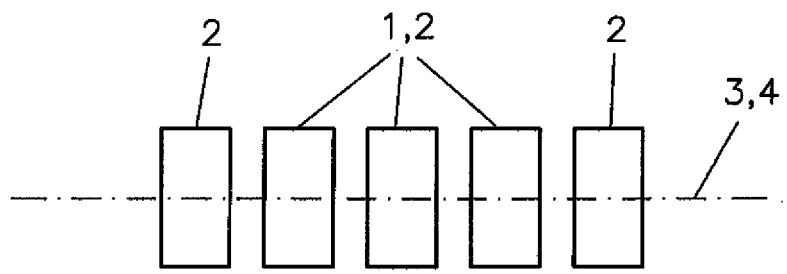
Figure 1C:
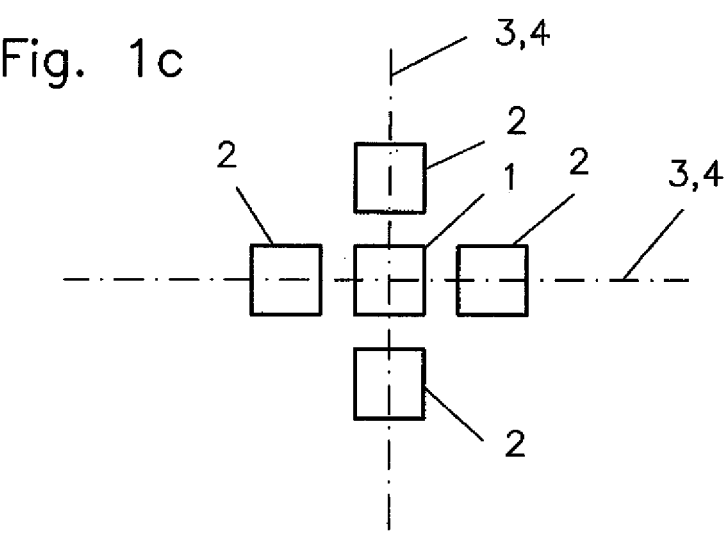

Essential elements of the sensor system are the sensors 17 with a fundamental electrode arrangement as it is shown in FIGS. 1a to 1c in an exemplar but not limiting manner.

They comprise in each case an arrangement as shown in FIG. 1a with an intermediate electrode 1 (reference electrode) as well as at least two measuring electrodes 2 which are arranged aligned at opposite sides of the reference electrode 1. The arrangement of the measuring electrodes 2 is preferably symmetrical with regard to the intermediate electrode 1 and all are preferably arranged in a single plane symmetrically around an axis of symmetry 3 representing the orientation 4 of the sensor.

In an embodiment of the sensor system 17 as shown for example in FIG. 1b, more than three electrodes, for example five electrodes are arranged in a row around the axis of symmetry. This permits a free selection of the three adjacent electrode surface areas comprising a center electrode (reference electrode) and two adjacent aligned measuring electrodes for determining potential differences. This embodiment furthermore permits the use of more than two measuring electrodes around the reference electrode and also, in a particularly advantageous manner, the selection during operation of the number of measuring electrodes or a switch of the use of the electrodes as intermediate or center electrode.

Preferably to selection of the three electrodes is made by a signal processing arrangement wherein preferably a switch-over is initiated by a deviation between potential differences determined by the sensor (for example, upon exceeding a programmable limit). In this connection, it is advantageous if all electrodes have a surface area which is uniform and extends symmetrically around the axis of symmetry as well as the same distance from one another. With the arrangement as shown in FIG. 1b, the sensor can remain operational, particularly upon occurrence of system and measuring disturbances simply by the selection and switch-over of the control of the electrodes as reference and measuring electrodes without the need of a new application or replacement.

FIG. 1c shows a sensor 17 with measuring electrodes 2 around, a reference electrode 1 along two axes of symmetry arranged cross-wise. The two axes of symmetry indicate the two orientations of the sensor.

Figure 2:
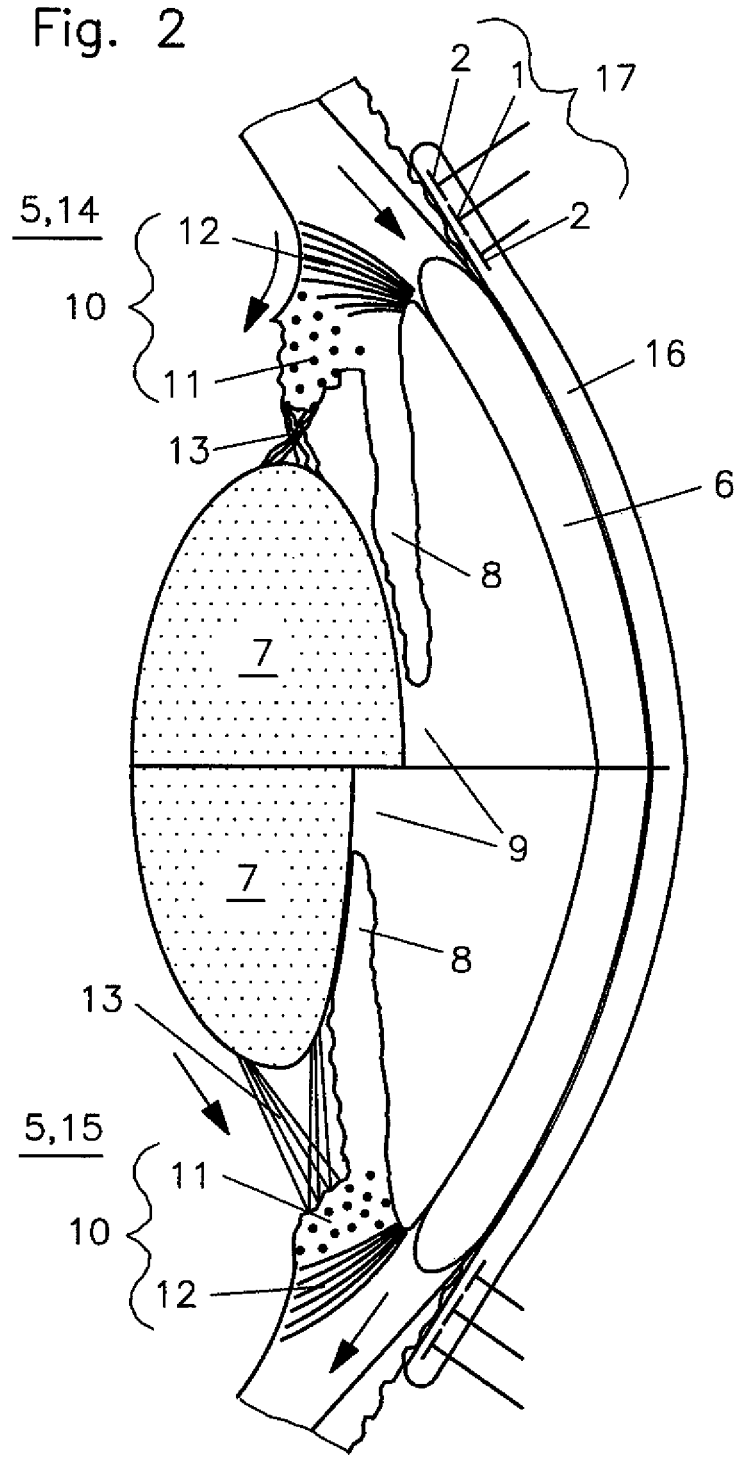
FIG. 2 is a partial cross-sectional view of an eye with a sensor system applied in the area of the pupil showing the ciliary muscle and signal sensing arrangement.

FIG. 2 shows schematically a part of the eye with applied sensor systems including electrodes in a cross-sectional view. The front part of the eye 5 as shown comprises the cornea 6, the lens 7, the iris muscle 8, the pupil 9 and the ciliary muscle 10. The ciliary muscle 10 comprises the Müller muscle 11 and the Brück muscle 12. The representation of the eye section is divided into two halves wherein the upper half and the lower half show the eye at different accommodation states of the natural optical system. The deformation of the lens and the ciliary muscle connected to the lens by zonula fibers 13 is clearly visible. The upper area 14 represents a near view adjustment; the lower area 15 represents a far view adjustment.

On the cornea 6, a contact lens 16 is disposed as contact element and carrier of the sensors 17. The contact element 16 has an annular area 18 around the iris or respectively, the pupil which area is disposed over, and adjacent to, the ciliary muscle and on which the sensors 17 are arranged in direct contact with the cornea 6. The signal processing arrangement which is not shown in FIG. 2 comprises electronic components and is arranged preferably on the annular area of the contact element or is integrated into the contact element in the area above the iris. The central area of the contact lens above the pupil comprises preferably an integrated lens system (not shown in FIG. 2) for example an artificial accommodation system with a lens system whose focal length is adjustable by the sensor system.

The electrodes are preferably arranged along the outer edge of the contact lens and sense there the potential changes generated by the muscle activity. At the outer edge of the contact lens, the distance from the ciliary muscle whose signal is to be detected is only small so that the amplitude of the ciliary muscle signal is substantially larger than that of signals of other muscles (for example, the iris muscles) which, at this point, are more remote from the electrodes.

FIGS. 3a-3d disclose selected exemplary embodiments of the sensor arrangement and orientation of the sensor system. They show a front view of the contact lens 16 wherein the eye 5 is shown schematically in the area thereof between the upper eye lid 22 and the lower eye lid 23.

Figure 3A:
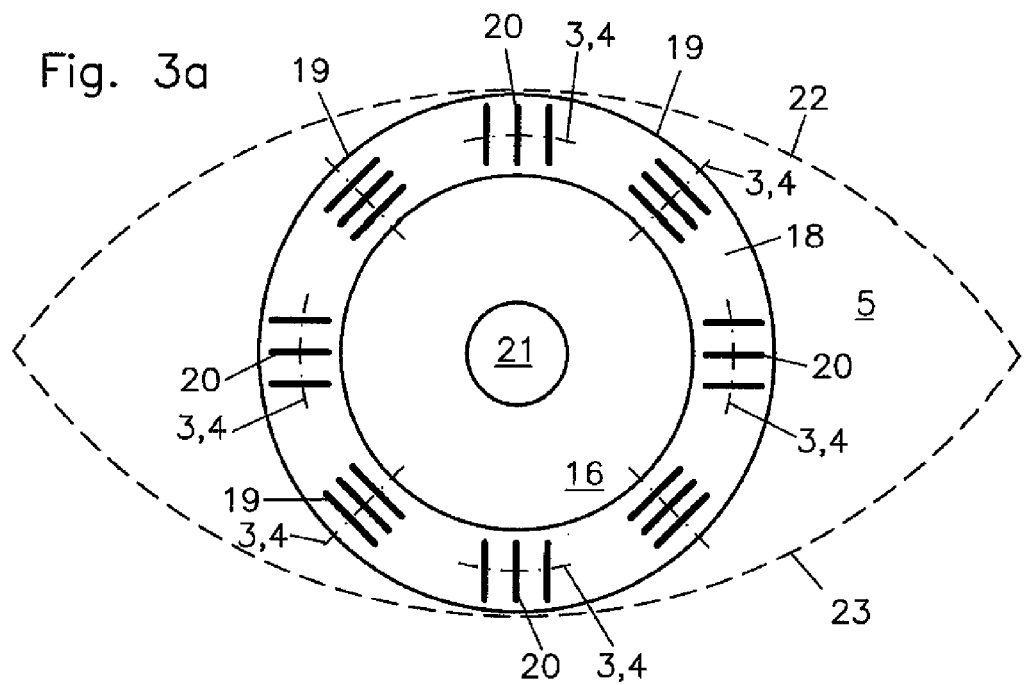
FIGS. 3a, 3b, 3c, 3d, 3e and 3f are schematic representations of embodiments of the sensor system with annular electrode arrangements.

A particularly preferred embodiment as shown in FIG. 3a comprises, in addition to the at least four sensors disposed in a radial array 19 with regard to the central pupil area 21, at least four sensors in a tangential array 20 which arrays are preferentially arranged alternately in the annular area 18 and concentrically with respect to, and around, the iris. The Müller muscle is an annular muscle whose control signal can be detected at any point of the annular area in a sufficiently secure way. The Brück muscle on the other hand extends radially with respect to the iris. A muscle fiber of this muscle can be detected only by a sensor disposed directly above that muscle, so that the control signal for this muscle can be detected only at a particular location of the annular area. In addition, the Müller muscles are arranged only at the inside of the ciliary body, whereas the Brück muscles are disposed further to the outside of the ciliary body. As a result of the position of the Müller muscles at the inner edge of the ciliary body the distance of the Müller muscles from the sensor electrodes is greater than that of the Brück muscles. In particular for increasing the signal-noise-distance of the tangential electrodes, it is advantageous to arrange specifically the sensors with the tangential array in a larger number redundantly distributed over the annular area. The embodiment represents an exemplary sensor system, wherein the sensors comprise electrodes arranged in at least two orientations which are tangentially as well as radially oriented with respect to the iris. By providing several measuring locations, the signal-to-noise ratio (SNR) can be noticeably increased.

Figure 3B:
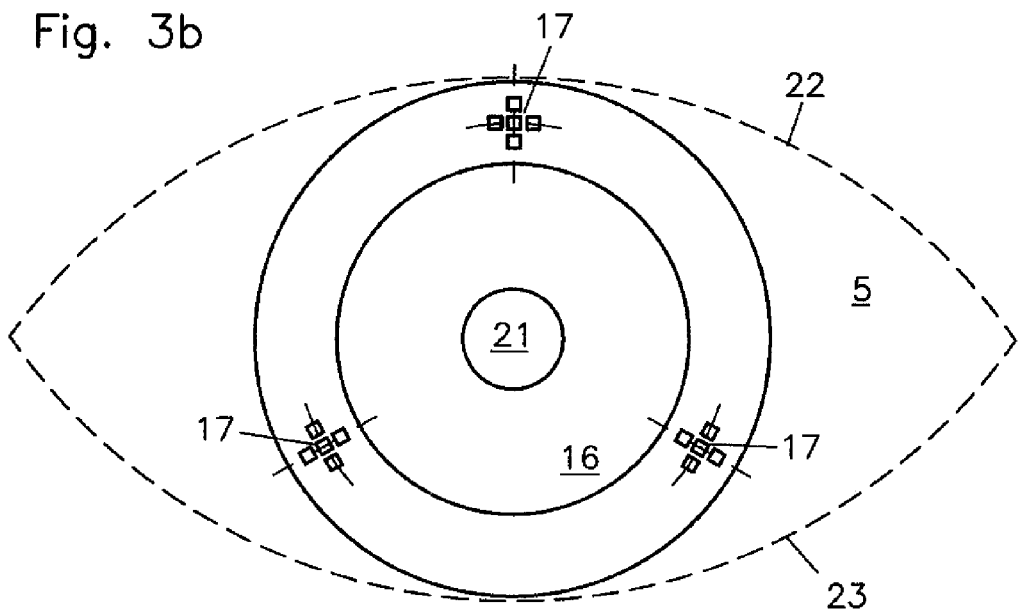

A combination of radially and tangent tally oriented electrodes results in a cross-shaped arrangement of electrodes of the sensors (see FIG. 1c). Preferably, in a particular embodiment at least three sensors are arranged in the annular area around the iris (FIG. 3b).

Figure 3C:
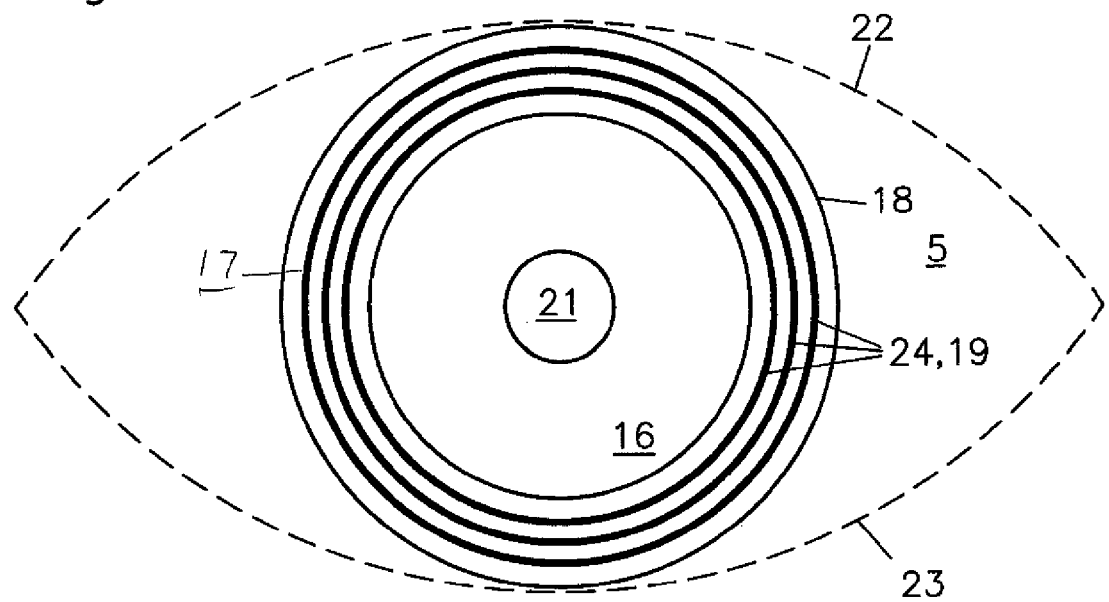

FIG. 3c shows another exemplary embodiment with a sensor arrangement 17 including at least three, preferably exactly three, electrode rings 24 which are arranged in the annular area concentrically with respect to the iris and preferably parallel to one another. An intermediate electrode ring serves as ground (reference potential). The electrode rings are in a preferred embodiment in the form of uninterrupted rings. The array orientation of these sensors is radial with respect to the central pupil area 21 that is, with regard to the pupil and the iris. This sensor detects Brück muscle fiber control signals in every angular area of the whole annulus and is particularly advantageous if individual Brück muscles are already damaged by sickness, infarcts, or paralysis. For determining the control signals, it is sufficient if a single healthy Brück muscle is covered by the electrode.

Figure 3D:
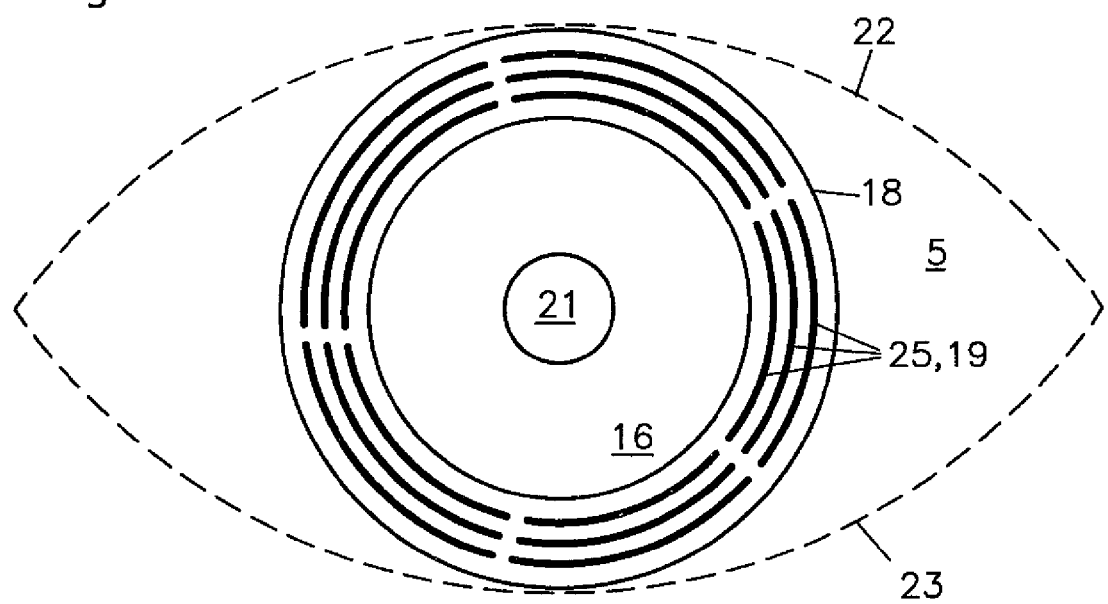
Figure 3E:
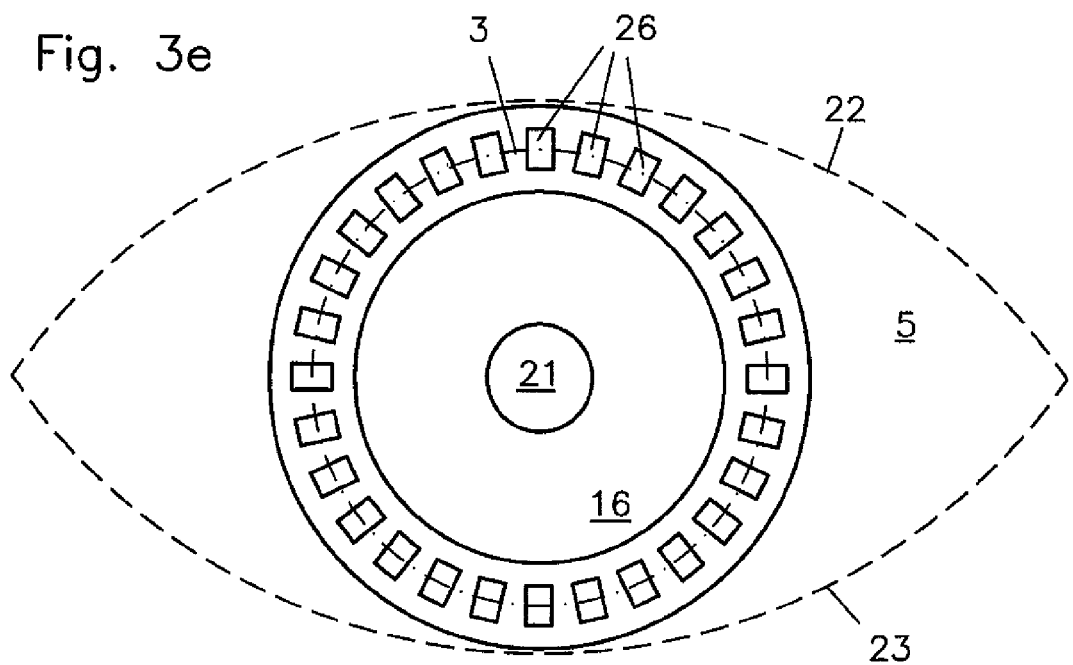

In a further exemplary embodiment as shown in FIG. 3d, the annular electrodes are divided into circular sections 25 which, in each case, cover an angular section around the iris. This facilitates a selective determination of the Brück muscle signals for each annular section and consequently the recognition and surveillance for example of changing pathological conditions such as sickness or health condition patterns in the respective angular sections, all angular sections being covered by a signal summation. The sensor system may optionally be combined with a sensor system including tangential arrays of sensors which however would be provided on a separate second annular area. By comparative measurements of adjacent sensor, additionally differences in the control the Brück muscles or also a displacement of the contact elements on the eye are detectable.

A particular embodiment in this regard proposes to provide a preferably annularly extending ring of electrodes with a plurality of individual electrodes 26 with tangential axis of symmetry 3 and orientation (FIG. 3c). Preferably, all electrode areas are in wired communication with the signal processing arrangement. In this embodiment, any three adjacent electrodes can be chosen and switched to form a sensor group as desired without changing the arrangement that is solely by individually controlling the electrode areas via the signal processing arrangement. In a particular variant at least three electrode groups are to be activated concurrently which electrode groups are preferably arranged at the same distance from one another evenly distributed over the circumference of the ring of electrodes. In this way, the control signals of the Müller muscles are determined at three locations wherein the values after optional elimination of erroneous measurements are preferably averaged. The occurrence of erroneous measurements preferably causes the signal processing arrangement to select a new electrode group at another location, that is, a displacement of the sensors on the Müller muscles.

Figure 3F:
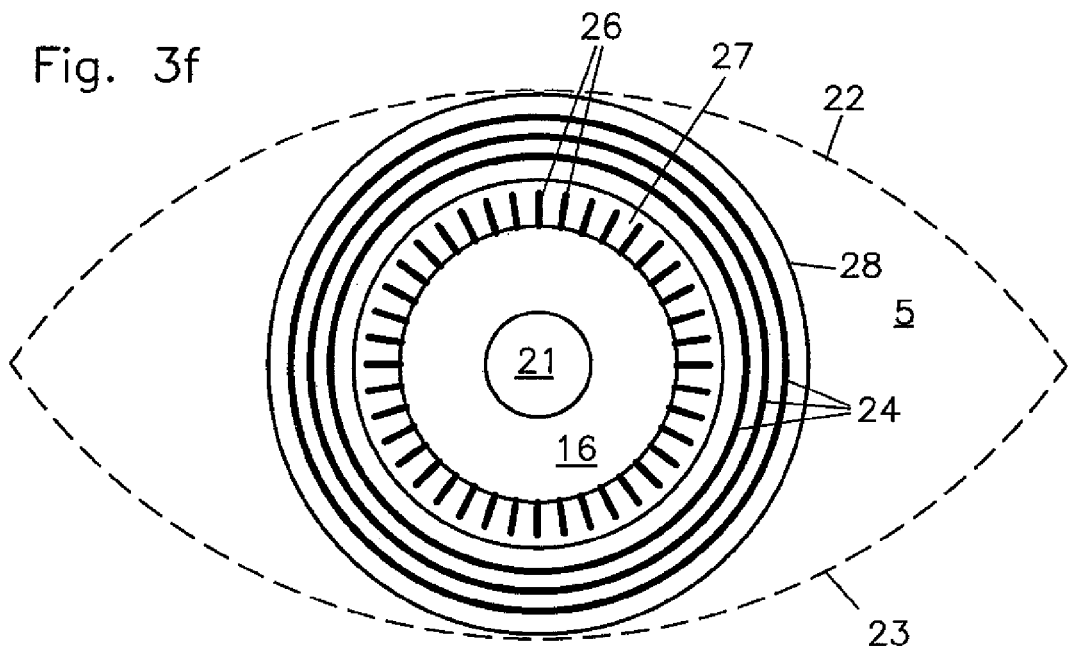

In another embodiment, the annular area is divided into two or several partial ring areas, wherein each annular area (see FIG. 3f) is preferably, but not necessarily, equipped with sensors of only one orientation. As shown in the exemplary embodiment of FIG. 3f, in the inner annular sensor area 27, an electrode ring with a multitude of individual electrodes is arranged along a circle of symmetry (see FIG. 3c) for determining the Müller muscle activation signals and also an outer electrode ring 28 with annular electrodes for determining the Brück muscle activation signals is provided (see FIG. 3c or 3d).

Basically, the electrodes are arranged with their axes of symmetry extending preferably radially or tangentially. By the radially oriented electrodes mainly actuation signals are detected which result from the radially extending muscle fibers (Brück muscle). It can be expected that in the radial signal also part of the iris activity is included. The tangential arrangement of the electrodes however results mainly in the detection of the signals of the tangentially extending muscle fibers (Müller muscles) of the ciliary body. In the process, the influence of the iris muscle signals is much reduced. For smoothening the reference potential all reference electrodes of the various measuring locations are interconnected. It is therefore advantageous that the radial electrode arrays are arranged at the outer partial annular area and the tangentially oriented arrays of electrodes are arranged preferably on the inner partial annular electrode area. This arrangement also meets the anatomy of the eye, since the Müller muscles are—like the tangential electrodes—arranged further to the inside and the Brück muscles as well as the radial electrodes are arranged further to the outside.

The sensor system 40 comprises furthermore a signal processing arrangement 39 including evaluation electronics integrated preferably also on the contact lens. The signal processing arrangement includes a signal conditioning unit 29 and an evaluation unit 30 with signal recognition and a generator for providing a control signal 31. Hot shown is an energy source for the sensor system such as a capacitive energy buffer which is charged by movements of the system in the earth magnetic field, by inertia generators or eye lid movement generators. Alternatively, a contact-free transmission of the required energy from without is possible for example via electromagnetic transmission means. Furthermore, solar cells may be used which convert the ambient light into electric energy or bio-fuel cells may be used which convert the chemical energy of the glucose of tear liquid into electric energy.

The evaluation electronics is to process the potential difference of low amplitude between the electrodes in such a way that the accommodation can be calculated. The measuring electrodes 2 of the sensors disposed adjacent the intermediate electrode 1 (reference potential for example based on ground) are connected to the signal conditioning unit 29 via electric conductors, preferably conductor strips, and supply the measurement signal in the signal conditioning unit 29 first to an ESD protection circuit 32. In this way, during common handling of the contact lens (insertion, removal, cleaning) by the user, damage to the electronics by electrostatic discharges are prevented. An ESD protection arrangement protects the evaluation unit in particular during handling by the system carrier during insertion, removal and cleaning of the systems from excessive voltages. Then a one or multi-stage amplifier circuit 33 follows in order to increase the amplitude of the signal. With a bi- or multi-polar configuration it is possible to suppress in phase interference voltages by a differential stage, which is preferably formed by an instrument amplifier. Subsequently, the signal is filtered in filter 34. Disturbances and high frequency noise are suppressed preferably in several filter stages followed by a rectifier circuit 35 in which the AC signal is converted to a DC signal which is proportional to the muscle activity. In order to be able to utilize for the detection the positive as well as the negative signal components, the use of a full wave rectifier is preferred. The processed rectified measuring signal is transmitted to the evaluation unit.

The preferably two voltage detected in a sensor are optionally averaged or weighted in the evaluation unit for example by a substractor and/or filter which processes the signals of certain electrodes which have already been processed. For example, in particular, measuring signals in the area near another adjacent muscle whose signals are not to be determined, are still influenced by the signals of the adjacent muscle. This interference influence can be recognized by a comparison of redundant measurement signals (generally two) which are determined by several electrodes of a sensor and eliminated in the evaluation unit. In this way, also an improved separation of tangential and radial muscle signals can be achieved and for example the iris muscle signal (radial) in the tangential ciliary muscle signal can be suppressed.

The evaluation unit 30 determines from the height of the processed rectified measuring signal relative to the reference potential the accommodation need and generates the control signal 31. In an arrangement with several measurement locations, the measuring signals are preferably additionally averaged or weighted in order to reduce the effects of extraneous undesirable muscle signals (for example, iris muscle signals) on the evaluation.

The control signal 31 is used for the setting of the focal length of an adjustable lens system and is transmitted to the lens system by transmission means (conductors or contact-free via electromagnetic waves). Alternatively, the above-mentioned processed and rectified measuring signal is supplied via the above-mentioned transmission means in a contact-free manner for example to a central evaluation unit for both eyes.

Optionally an offset correction or calibration may foe performed. To this end, user-specific calibration data 38 are transmitted via a communication interface 36 to an external computer 37 to the evaluation unit 30. As a result, the system can be rapidly adapted to an individual user in an optimal manner.

Literature:
[1] Strenk, B. et al., Age-related changes in human ciliary muscle and lens: A magnetic resonance imaging study: Investigative Opthalmology and Visual Sci. 40 (1999, 6 page 1162-1169).
[2] SP 1 919 360 B1
[3] Klink S: Neues System zur Erfassung des Akkommodationsbedarfs im menschlichen Ange, Schriftenreihe des Instituts für angewandte Informatik/Automationstechnik der Universität Karlsruhe (TH), edition 23 Universitätsverlag Karlsruhe, 2008, ISBN 978-3-86644-300-6.
[4] U.S. Pat. No. 4,386,831
[5] RU 2 281 020 C1
[6] U.S. Pat. No. 7,404,636 B2
[7] U.S. Pat. No. 6,851,805 B2
[8] DE 10 2005 038 542 A1

| Listing of Reference Numerals: | |
|---|---|
| 1 | Intermediate sensor electrode |
| 2 | Measuring electrode |
| 3 | Axis of Symmetry |
| 4 | Orientation |
| 5 | Eye |
| 6 | Cornea |
| 7 | Lens |
| 8 | Iris muscle |
| 9 | Pupil |
| 10 | Ciliary muscle |
| 11 | Muller muscle |
| 12 | Bruck muscle |
| 13 | Zenular lens |
| 14 | Upper area |
| 15 | Lower area |
| 16 | Contact lens |
| 17 | Sensor |
| 18 | Annular area |
| 19 | Sensor with radial array |
| 20 | Sensor with tangential array |
| 21 | Pupil area |
| 22 | Upper eye lid |
| 23 | Lower eye lid |
| 24 | Electrode rings |
| 25 | Circular section |
| 26 | Individual electrode |
| 27 | Inner circular section area |
| 28 | Outer circular section area |
| 29 | Signal conditioning |
| 30 | Evaluation unit |
| 31 | Control signal |
| 32 | ESD-protection circuit |
| 33 | Amplifier circuit |
| 34 | Filter |
| 35 | Rectifier circuit |
| 36 | Communication interface |
| 37 | Computer |
| 38 | Calibration data |
| 39 | Signal processing arrangement |
| 40 | Sensor system |

What is claimed is:

1. A sensor system for determining control signals of a ciliary muscle of an eye having a cornea, a lens a pupil, an iris, ciliary muscles, comprising Müller muscles, and Brück muscles and zenular fibers, the sensor system comprising:
   a) a contact element consisting of an electrically non-conductive material for disposition on the cornea in contact with the area of the eye around the iris thereof,
   b) a sensor system with at least one sensor applied to the contact element in an annular array around the iris, and
   c) a signal processing arrangement disposed on, or in, the contact element,
   d) each sensor comprising at least three electrodes oriented in the same direction and arranged in a row,
   e) the orientations comprising at least one orientation extending in a radial direction with respect to the iris and
   f) each sensor having an intermediate electrode which forms a reference potential and two electrodes which are disposed in the orientation direction directly adjacent to, and at opposite sides of, the intermediate electrode and which determines an eye body potential with respect to the reference potential.

2. The sensor system according to claim 1, wherein the at least one sensor is arranged on an annular surface area of the contact element around the iris.

3. The sensor system according to claim 2, wherein at least two sensors are provided which have orientations in tangential as well as radial directions with respect to the iris.

4. The sensor system according to claim 3, wherein each sensor has either only a tangential or a radial orientation with respect to the iris and the sensors are arranged on the annular surface area with alternate orientations.

5. The sensor system according to claim 1, wherein the sensor comprise at least four measuring electrodes arranged around a center electrode in tangential and also in radial orientations with respect to the iris.

6. The sensor system according to claim 2, wherein a sensor comprises as electrodes three electrode rings or ring sections arranged on the annular surface area concentrically with respect to the iris.

7. The sensor system according to claim 1, wherein at least four sensors with tangential orientation are provided.

8. The sensor system according to claim 1, wherein the contact element is a contact lens.

9. The sensor system according to claim 1, wherein the signal processing arrangement comprises a signal conditioning unit and a signal recognition unit with a generator for generating a control signal.

10. The sensor system according to claim 9, wherein the system includes a lens system or lens with an adjustable focal length and the signal processing arrangement includes transmission means for transmitting the control signal to the lens system or lens for adjusting the focal length thereof depending on the control signal.

* * * * *